United States Patent [19]

Kaeding et al.

[11] Patent Number: 4,929,790
[45] Date of Patent: May 29, 1990

[54] CATALYTIC CONVERSION OF PROPANE TO ETHYLENE OVER ZSM-23

[75] Inventors: Warren W. Kaeding, Lawrenceville, N.J.; Ernest W. Valyocsik, Yardley, Pa.

[73] Assignee: Mobil Oil Corporation, New York, N.Y.

[21] Appl. No.: 217,112

[22] Filed: Jul. 7, 1988

Related U.S. Application Data

[63] Continuation of Ser. No. 784,966, Oct. 7, 1985, abandoned.

[51] Int. Cl.$^5$ .................................................. C07C 4/06
[52] U.S. Cl. ...................................... 585/651; 585/648; 208/120
[58] Field of Search ...................... 585/650, 651, 6 XP; 208/120

[56] References Cited

U.S. PATENT DOCUMENTS

| | | | |
|---|---|---|---|
| 3,668,268 | 6/1972 | Mulaskey | 260/676 |
| 3,668,269 | 6/1972 | Chloupek | 260/676 R |
| 3,760,024 | 9/1973 | Cattanach | 260/673 |
| 3,812,199 | 5/1974 | Chen et al. | 260/676 R |
| 3,972,832 | 8/1976 | Butter et al. | 252/437 |
| 4,076,842 | 2/1978 | Plank et al. | 423/328 |
| 4,104,151 | 8/1978 | Rubin et al. | 585/512 |
| 4,490,342 | 12/1984 | Valyocsik | 423/328 |
| 4,554,260 | 11/1985 | Pieters et al. | 502/61 |
| 4,665,251 | 5/1987 | Chu | 585/415 |
| 4,686,316 | 8/1987 | Morrison | 585/708 |

FOREIGN PATENT DOCUMENTS 0174121  3/1986  European Pat. Off. .

OTHER PUBLICATIONS

*Applied Catalysis*, 19 (1985), 153-163, "Reactions of Propane Over a Bifunctional Pt/H-ZSM-5 Catalyst".

*Primary Examiner*—Asok Pal
*Attorney, Agent, or Firm*—A. J. McKillop; C. J. Speciale; E. F. Kenehan, Jr.

[57] ABSTRACT

There is provided a process for converting propane to ethylene over a zeolite catalyst comprising ZSM-23. This zeolite may be contacted with an anhydrous acidic oxide gas capable of accepting hydrogen by reacting therewith, such as sulfur dioxide ($SO_2$), in order to enhance the ethylene selectivity of the conversion. The zeolite may either be pretreated with this acidic oxide gas or contacted in situ by cofeeding the acidic oxide gas along with the propane reactant. Particularly in view of the tendency of zeolites such as ZSM-5 to further convert olefins produced into aromatics and other hydrocarbons, the large degree of ethylene selectivity achieved by the process of the present invention is surprising.

13 Claims, No Drawings

CATALYTIC CONVERSION OF PROPANE TO ETHYLENE OVER ZSM-23

This is a continuation of copending application Ser. No. 784,966, filed on Oct. 7, 1985, now abandoned.

CROSS-REFERENCE TO RELATED APPLICATIONS

This application is related to copending U.S. application Ser. No. 642,961, filed Aug. 21, 1984, now abandoned, which discloses the conversion of propane to light olefins and aromatics over a zeolite designated as ZSM-57.

This application is also related to copending U.S. application Ser. No. 784,967, filed Oct. 7, 1985, which discloses the conversion of propane to ethylene over ZSM-50.

The entire disclosures of these cross-referenced applications are expressly incorporated herein by reference.

BACKGROUND

Ethylene is prepared commercially by heating ethane, propane, higher paraffins or naphtha, diluted with steam, at about 850° C., 1550° F., for very short contact times, without a catalyst. Highest ultimate yields come from ethane (81%), propane (43%) and n-butane (41.5%). All world-scale plants with billion-pound-per-year ethylene capacity are based on this thermal cracking/dehydrogenation technology. Although a host of rival schemes has been studied, none have reached commercial application.

Weaknesses in the established process are (1) high reaction temperature and low hydrocarbon partial pressure, (2) low product separation/purification temperatures (−150° to −200° F.) and high pressure (500 psig), (3) relatively low yields from $C_3$ and higher feeds, (4) a complex mixture of products, and (5) relatively high capital and operating costs.

SUMMARY

According to one aspect of the invention, there is provided a process for converting propane to ethylene, said process comprising contacting said propane with a catalyst comprising ZSM-23 under sufficient conversion conditions.

EMBODIMENTS

ZSM-23 is described in U.S. Pat. Nos. 4,076,842 and 4,490,342, the entire disclosures of which are expressly incorporated herein by reference.

The synthetic ZSM-23 zeolite possesses a definite distinguishing crystalline structure whose X-ray diffraction pattern shows substantially the significant lines set forth in Table I.

TABLE I

| d(A) | $I/I_o$ |
| --- | --- |
| 11.2 ± 0.23 | Medium |
| 10.1 ± 0.20 | Weak |
| 7.87 ± 0.15 | Weak |
| 5.59 ± 0.10 | Weak |
| 5.44 ± 0.10 | Weak |
| 4.90 ± 0.10 | Weak |
| 4.53 ± 0.10 | Strong |
| 3.90 ± 0.08 | Very Strong |
| 3.72 ± 0.08 | Very Strong |
| 3.62 ± 0.07 | Very Strong |
| 3.54 ± 0.07 | Medium |
| 3.44 ± 0.07 | Strong |
| 3.36 ± 0.07 | Weak |
| 3.16 ± 0.07 | Weak |
| 3.05 ± 0.06 | Weak |
| 2.99 ± 0.06 | Weak |
| 2.85 ± 0.06 | Weak |
| 2.54 ± 0.05 | Medium |
| 2.47 ± 0.05 | Weak |
| 2.40 ± 0.05 | Weak |
| 2.34 ± 0.05 | Weak |

The above values were determined by standard techniques. The radiation was the K-alpha doublet of copper, and a scintillation counter spectrometer with a strip chart pen recorder was used. The peak heights, I, and the positions as a function of 2 times theta, where theta is the Bragg angle, were read from the spectrometer chart. From these, the relative intensities, 100 $I/I_o$, where $I_o$ is the intensity of the strongest line or peak, and d(obs.), the interplanar spacing in Angstrom units, corresponding to the recorded lines, were calculated. It should be understood that this X-ray diffraction pattern is characteristic of all the species of ZSM-23 compositions. Ion exchange of the sodium ion with cations reveals substantially the same pattern with some minor shifts in interplanar spacing and variation in relative intensity. Other minor variations can occur depending on the silicon to aluminum ratio of the particular sample, and on whether it has previously been subjected to thermal treatment.

ZSM-23 may have a formula, in terms of mole ratios of oxides, as follows:

$$(0-2)M_{2/n}O:(0-5)Al_2O_3:100SiO_2$$

wherein M is a cation of valance n (e.g., alkali metal or alkaline earth metal cations).

In accordance with the present invention, the zeolite catalyst may be contacted with an anhydrous acidic oxide gas capable of accepting hydrogen by reacting therewith. Examples of such gases include oxidative dehydrogenation agents such as sulfur dioxide ($SO_2$) and nitrous oxide ($N_2O$). Such oxide gases may be contacted with the zeolites by a pretreatment procedure, e.g., prior to any catalytic use, or as a cofeed with the propane reactant.

The zeolites suitable for use in accordance with the present invention may be combined with another material resistant to the temperatures and other conditions employed in the present organic conversion process. Such matrix materials include active and inactive materials and synthetic or naturally occurring zeolites as well as inorganic materials such as clays, silica and/or metal oxides, e.g. alumina. The latter may be either naturally occurring or in the form of gelatinous precipitates, sols or gels including mixtures of silica and metal oxides. Use of a material in conjunction with the zeolite, i.e. combined therewith, which is active, may enhance the conversion and/or selectivity of the catalyst in certain organic conversion processes. Inactive materials suitably serve as diluents to control the amount of conversion in a given process so that products can be obtained economically and orderly without employing other means for controlling the rate or reaction. Frequently, crystalline silicate materials have been incorporated into naturally occurring clays, e.g. bentonite and kaolin. These materials, i.e. clays, oxides, etc., function, in part, as binders for the catalyst. It is desirable to provide a catalyst having good crush strength, because in use the catalyst may be subjected to rough handling, which tends to break the catalyst down into powder-like materials which cause problems in processing.

Naturally occurring clays which can be composited with the zeolite include the montmorillonite and kaolin families which include the subbentonites, and the kaolins commonly known as Dixie, McNamee, Georgia and Florida clays, or others in which the main mineral constituent is halloysite, kaolinite, dickite, nacrite or anauxite. Such clays can be used in the raw state as originally mined or initially subjected to calcination, acid treatment or chemical modification.

In addition to the foregoing materials, the zeolite catalyst hereby synthesized can be composited with a porous matrix material such as silica-alumina, silica-magnesia, silica-zirconia, silica-thoria, silica-beryllia, silica-titania, as well as ternary compositions such as silica-alumina-thoria, silica-alumina-zirconia, silica-alumina-magnesia and silica-magnesia-zirconia. The matrix can be in the form of a cogel. A mixture of these components could also be used. The relative proportions of finely divided crystalline silicate and matrix vary widely with the crystalline silicate content ranging from about 1 to about 90 percent by weight, and more usually in the range of about 2 to about 50 percent by weight of the composite.

Conditions for converting propane in accordance with the present invention may include a temperature of from about 100° C. to about 700° C., a pressure of from about 0.1 atmosphere to about 60 atmospheres, and a weight hourly space velocity of from about 0.5 to about 400. The feedstock, in addition to propane, may optionally comprise, e.g., up to about 98% of a diluent gas, especially an inert diluent gas. The feedstock may also comprise a small percentage, e.g., 1 percent by weight or less, of impurities associated with propane feedstocks such as butane.

Although ZSM-23 has been found to be particularly suited for converting propane to ethylene in accordance with the present invention, it is possible that other molecular sieve catalysts may also be suitable for this purpose.

EXAMPLE 1

Zeolite ZSM-23 was synthesized with the diquaternary ammonium salt Diquat-7 dibromide [Br(CH$_3$)$_3$N(CH$_2$)$_7$N(CH$_3$)$_3$Br]. The aluminosilicate hydrogel was prepared according to the procedure described in Example 1 of U.S. Pat. No. 4,490,342. This hydrogel was transferred to a stainless steel autoclave.

The reaction mixture in the autoclave was stirred at autogenous pressure for 5 days at 160° C. At the end of this period, the autoclave was quenched in an ice bath to terminate the crystallization. The crystalline product was filtered, washed with deionized water, then dried.

X-ray diffraction analysis of the crystalline product showed the material to be 100% crystalline zeolite ZSM-23. From chemical analysis of this product SiO$_2$/Al$_2$O$_3$=40.8. SEM photos of the ZSM-23 crystals showed that their sizes ranged 0.1-0.2 μm.

EXAMPLE 2

The synthesis of this ZSM-23 material was conducted in essentially the same manner as Example 1 except that the SiO$_2$/Al$_2$O$_3$ ratio of the hydrogel was adjusted to 150.

The autoclave was stirred at autogenous pressure for three days at 160° C. before quenching in an ice bath.

X-ray powder diffraction analysis of this dried zeolite product showed it to be 100% crystalline ZSM-23. SEM examination of the ZSM-23 crystals revealed their sizes ranged 0.5-1.5 m. The chemical analysis of the zeolite gave SiO$_2$/Al$_2$O$_3$=145.

EXAMPLE 3

This HZSM-23 zeolite catalyst was crystallized with a pyrrolidine/ethanol mixture (7:6 wt ratio) in a thirty gallon autoclave at 320° F. in 48 hours. The zeolite was processed using precalcination (in nitrogen/1000° F.), ammonium nitrate exchange, and final calcination (in air/1000° F.) procedures. The chemical and sorption results are as follows:

| | |
|---|---|
| Crystallinity | 70% by X-ray |
| SiO$_2$/Al$_2$O$_3$ | 80/1 |
| C wt % | 0.005 |
| Na wt % | 0.01 |
| N ppm | 15 |
| Ash (1000° C.) | 96.64 |
| Adsorption Capacity, wt % | |
| Cyc C$_6$ | 4.1 |
| N C$_6$ | 6.6 |

EXAMPLE 4

The ZSM-23 samples, synthesized by the methods of Examples 1 and 2, were calcined at 550° C. and NH$_4$$^+$-exchanged in NH$_4$Cl in the same manner.

After NH$_4$$^+$-exchange, the zeolite was filtered, washed with deionized water to remove excess NH$_4$Cl, then finally dried in an air stream under an infrared heat lamp.

In Examples which follow, the zeolites of the previous Examples were used to convert propane.

Reagent grade propane containing 0.9% n-butane was used without further purification. Corrections were made for the butane in runs with low conversion. Five to ten grams of pressed wafers of catalyst, crushed and screened to 14-20 mesh, were used in glass screening reactors. Effluent gas was sampled in a hot syringe and analyzed for hydrocarbon. A second sample was analyzed with an argon carrier gas to measure hydrogen. Material balances of ±5% were usually obtained.

When sulfur dioxide was used, it was used in accordance with the following procedure:

A. Sulfur dioxide, 20 cc/min, was passed over the catalyst for 30-60 min at 300° C., followed by calcination in air for 30-60 min at 500° C.

B. After treatment of the catalyst as described in A, above, 1-3 wt % SO$_2$ was added to the propane feed for the screening reaction.

Accordingly, sulfur dioxide, SO$_2$, was used to modify the catalyst. It was also added to the propane feed to determine whether it would function as a hydrogen acceptor, producing hydrogen sulfide and water, and thereby increase conversion and selectivity, Equations 1 and 2. Surprisingly, ethylene was the major product, rather than propylene. The large amount of methane produced suggested the well-known cracking reaction to give these products, Equation 3.

$$CH_3CH_2CH_3 \rightleftharpoons CH_3CH=CH_2 + H_2 \qquad (1)$$

$$3CH_3CH_2CH_3 + SO_2 \rightarrow 3CH_3CH=CH_2 + H_2S + 2H_2O \qquad (2)$$

$$CH_3CH_2CH_3 \rightarrow CH_2=CH_2 + CH_4 \qquad (3)$$

The HZSM-23 of Example 3 was initially used in basic screening tests in accordance with the following Example 5.

EXAMPLE 5

The HZSM-23 of Example 3 was evaluated for the conversion of propane. This HZSM-23 had a $SiO_2/Al_2O_3$ molar ratio of 83/1.

Reaction conditions were varied to maximize ethylene selectivity and propane conversion. A dramatic increase in ethylene selectivity is observed by comparison with the unmodified catalyst. Selected runs are summarized in Table 2. In addition to ethylene and methane, propylene and butylene were also present in significant amounts. Liquid products were produced by further reactions of the olefins.

Catalyst aging was more rapid than observed with HZSM-5. The catalyst was regenerated by calcination with air every 2-5 hours to minimize the effect of coke.

EXAMPLE 6

The ZSM-23 of Example 2, as treated in accordance with Example 4, was evaluated for the conversion of propane. This HZSM-23 had a $SiO_2/Al_2O_3$ molar ratio of 145/1.

ZSM-23 with a higher silica/alumina ratio (145/1) was tested for comparison with the initial catalyst (83/1). Compared with the previous run, a larger number of reaction conditions were tested to establish a more significant base line prior to modification and use of sulfur dioxide (Method B). Detailed product selectivities for certain runs are shown in Tables 3 and 4.

A more modest but definite improvement in ethylene selectivity is observed with the use of $SO_2$ at comparable conversions (7–10%) in comparison with the previous run. Analysis of the gas stream indicated that all of the $SO_2$ was consumed. Hydrogen sulfide odor was detected in the product, but not quantified. The fate of the sulfur has not been completely determined. The overall selectivity to ethylene was best for the 83/1 silica/alumina catalyst, Example 5.

TABLE 2

Conversion of Propane to Ethylene
ZSM-23, $SiO_2/Al_2O_3$ 83/1, $SO_2$ Treated

| | Run No. | | | | | | | | | | | |
|---|---|---|---|---|---|---|---|---|---|---|---|---|
| | 1 | 2 | 3 | 4 | 5 | 6 | 7 | 8 | 9 | 10 | 11 | 12 |
| Temp. °C. | 500 | 550 | 550 | 550 | 550 | 600 | 600 | 600 | 600 | 600 | 600 | 650 |
| $SO_2$ Treatment | A | A | A | A | A | A | A | A | A | A | A | A |
| WHSV $C_3H_8$ | .864 | .864 | .864 | .864 | 3.46 | .864 | .864 | 1.73 | 2.59 | 3.46 | 3.46 | 3.46 |
| Conversion, wt % | 14 | 38 | 28 | 24 | 5 | 62 | 52 | 38 | 28 | 22 | 10 | 36 |
| Selectivity, wt % | | | | | | | | | | | | |
| BTX[B] | 2.2 | 6.8 | 2.6 | 2.4 | 0 | 9.9 | 7.7 | 3.7 | 1.9 | 1.2 | .4 | 2.9 |
| $C_9+$ | 1.0 | 1.2 | 1.6 | 1.4 | 0 | 2.1 | 1.7 | .7 | .2 | 0 | 0 | .1 |
| $H_2$ | .6 | .9 | .8 | .7 | .6 | 1.1 | 1.1 | 1.0 | .9 | .9 | .9 | 1.2 |
| $CO/CO_2$ | 0 | 0 | 0 | 0 | 0 | 0 | | | | | | |
| $CH_4$ | 30.9 | 31.8 | 31.4 | 30.2 | 27.3 | 31.5 | 30.8 | 30.9 | 30.7 | 30.6 | 29.4 | 29.3 |
| $C_2H_6$ | 5.9 | 5.8 | 5.1 | 4.7 | 1.8 | 4.7 | 4.3 | 3.3 | 2.5 | 2.1 | 1.6 | 2.3 |
| $C_2H_4$ | 30.9 | 24.4 | 32.7 | 36.0 | 44.8 | 25.2 | 29.9 | 36.9 | 42.5 | 44.8 | 46.3 | 41.8 |
| $C_3H_8$ | SM[C] | SM | SM | SM | SM | SM | SM | SM | SM | SM | SM | SM |
| $C_3H_6$ | 17.5 | 18.6 | 16.7 | 16.4 | 14.5 | 17.1 | 16.6 | 16.7 | 16.5 | 16.6 | 18.3 | 19.1 |
| $C_4H_{10}$ | 3.2 | 1.1 | .7 | 1.6 | 11.0 | .5 | .5 | .5 | .8 | 1.3 | 3.1 | .5 |
| $C_4H_8$ | 7.8 | 9.4 | 8.4 | 6.6 | 0 | 7.9 | 7.4 | 6.3 | 4.0 | 2.5 | 0 | 2.8 |
| Total | 100.0 | 100.0 | 100.0 | 100.0 | 100.0 | 100.0 | 100.0 | 100.0 | 100.0 | 100.0 | 100.0 | 100.0 |

A Catalyst treated with SO2 prior to use.
[B]Benzene, toluene and xylene.
[C]SM = starting material.

TABLE 3

Conversion of Propane to Ethylene
ZSM-23, $SiO_2/Al_2O_3$ 145/1, $SO_2$ Treated

| | Run No. | | | | | | |
|---|---|---|---|---|---|---|---|
| | 1 | 2 | 3 | 4 | 5 | 6 | 7 |
| Temp. °C. | 550 | 550 | 550 | 550 | 550 | 550 | 550 |
| WHSV | | | | | | | |
| $C_3H_8$ | .432 | .864 | 1.73 | 3.46 | .864 | 1.73 | 1.73 |
| $SO_2$ | 0 | 0 | 0 | 0 | .0056 | .011 | .011 |
| Conversion | 54 | 31 | 18 | 12 | 24 | 18 | 17 |
| Selectivity, wt % | | | | | | | |
| BTX[a] | 18.0 | 11.2 | 6.5 | 1.9 | 8.3 | 4.6 | 3.9 |
| $C_9+$ | 2.1 | 1.5 | 2.9 | 3.6 | 2.6 | 1.2 | .8 |
| Tot. Liq. Prod. | 20.1 | 12.7 | 9.4 | 5.5 | 10.9 | 5.8 | 4.7 |
| $H_2$ | 1.8 | 2.2 | 1.3 | 1.2 | 1.3 | 1.2 | 1.1 |
| $CO/CO_2$ | .3 | .2 | 0 | 0 | 2.5 | 3.2 | 3.2 |
| $CH_4$ | 36.6 | 32.7 | 27.6 | 26.5 | 27.7 | 27.0 | 27.1 |
| $C_2H_6$ | 10.4 | 7.5 | 4.4 | 2.9 | 5.5 | 4.5 | 4.0 |
| $C_2H_4$ | 12.1 | 19.6 | 30.1 | 37.3 | 28.8 | 33.1 | 35.3 |
| $C_3H_8$ | SM[b] | SM | SM | SM | SM | SM | SM |
| $C_3H_6$ | 11.3 | 16.2 | 19.1 | 19.8 | 16.5 | 18.8 | 18.5 |
| $C_4H_{10}$ | 2.4 | 2.4 | 2.4 | 4.4 | 2.1 | 2.8 | 2.9 |
| $C_4H_8$ | 5.0 | 6.5 | 5.7 | 2.4 | 4.7 | 3.6 | 3.2 |

TABLE 3-continued

Conversion of Propane to Ethylene
ZSM-23, $SiO_2/Al_2O_3$ 145/1, $SO_2$ Treated

| | Run No. | | | | | | |
|---|---|---|---|---|---|---|---|
| | 1 | 2 | 3 | 4 | 5 | 6 | 7 |
| Total | 100.0 | 101.9 | 100.0 | 100.0 | 100.0 | 100.0 | 100.0 |

(a) Benzene, toluene and xylene.
(b) SM = starting material.

TABLE 4

Conversion of Propane to Ethylene
ZSM-23, $SiO_2/Al_2O_3$ 145/1, $SO_2$ Treated

| | Run No. | | | | | | | |
|---|---|---|---|---|---|---|---|---|
| | 8 | 9 | 10 | 11 | 12 | 13 | 14 | 15 |
| Temp. °C. | 600 | 600 | 600 | 600 | 600 | 600 | 600 | 600 |
| | | | | | | B | B | B |
| WHSV | | | | | | | | |
| $C_3H_8$ | .864 | 1.73 | 1.73 | 3.46 | 6.91 | .864 | 1.73 | 1.73 |
| $SO_2$ | 0 | 0 | 0 | 0 | 0 | .006 | .0113 | .0113 |
| Conversion, wt % | 56 | 45 | 35 | 28 | 23 | 47 | 33 | 29 |
| Selectivity, wt % | | | | | | | | |
| BTX | 12.0 | 8.6 | 4.2 | 2.9 | 1.6 | 7.7 | 3.2 | 2.7 |
| $C_9+$ | 1.9 | .7 | 1.1 | .2 | 0 | 1.4 | .1 | .2 |
| Tot. Liq. Prod. | 13.9 | 9.3 | 5.3 | 3.1 | 1.6 | 9.1 | 3.3 | 2.9 |
| $H_2$ | 1.8 | 1.8 | 1.6 | 1.6 | 1.8 | 1.4 | 1.0 | 1.0 |
| $CO/CO_2$ | .1 | .1 | 0 | 0 | 0 | .7 | 1.2 | 1.2 |
| $CH_4$ | 30.3 | 29.6 | 27.9 | 26.2 | 23.8 | 30.2 | 28.9 | 28.7 |
| $C_2H_6$ | 6.3 | 5.8 | 3.9 | 3.6 | 3.4 | 5.4 | 3.6 | 3.2 |
| $C_2H_4$ | 23.8 | 27.1 | 34.0 | 35.1 | 33.9 | 30.3 | 37.5 | 38.6 |
| $C_3H_8$ | SM | SM | SM | SM | SM | SM | SM | SM |
| $C_3H_6$ | 16.5 | 18.9 | 20.9 | 25.2 | 30.4 | 16.6 | 18.5 | 18.8 |
| $C_4H_{10}$ | .4 | .9 | .9 | 1.2 | 2.1 | .6 | 1.3 | 1.6 |
| $C_4H_8$ | 6.9 | 6.5 | 5.5 | 4.0 | 3.0 | 5.5 | 4.7 | 4.0 |
| Total | 100.0 | 100.0 | 100.0 | 100.0 | 100.0 | 100.0 | 100.0 | 100.0 |

B Cofeed $SO_2$, treat with $SO_2$ first.

EXAMPLE 7

The ZSM-23 of Example 1, as treated in accordance with Example 4, with a $SiO_2/Al_2O_3$ ratio of 40.8/1 was tested for conversion of propane to ethylene. Results are summarized in Table 5. Initial runs with unmodified catalyst gave primarily aromatic and paraffinic products. Ethylene selectivities varied from only 4–13% in the 400°–600° C. temperature range. Although treatment with $SO_2$ reduced the activity and increased the selectivity to ethylene, overall performance was inferior to the previous runs.

TABLE 5

Conversion of Propane to Ethylene
HZSM-23, $SiO_2/Al_2O_3$ 40.8, $SO_2$ Treated

| | Run No. | | | | | | |
|---|---|---|---|---|---|---|---|
| | 1 | 2 | 3 | 4 | 5 | 6 | 7 |
| Temp. °C. | 550 | 550 | 550 | 550 | 600 | 600 | 600 |
| | A | A | B | A | A | B | B |
| WHSV | | | | | | | |
| $C_3H_8$ | .432 | 1.30 | 1.30 | 1.30 | .432 | 1.30 | 1.30 |
| $SO_2$ | | | .0105 | | | .021 | .0105 |
| Conversion | 64 | 45 | 31 | 18 | 82 | 42 | 33 |
| B Sel. | 1.9 | 2.7 | 2.5 | 1.2 | 3.7 | 3.3 | 2.5 |
| T | 5.3 | 3.3 | 2.0 | .7 | 7.1 | 2.0 | 1.5 |
| X | 6.9 | 6.0 | 4.5 | 1.6 | 8.6 | 3.5 | 2.8 |
| Total | 14.1 | 12.0 | 9.0 | 3.5 | 19.4 | 8.8 | 6.8 |
| $C_9+$ | 9.9 | 6.4 | 4.2 | 1.5 | 7.8 | 4.5 | 2.7 |
| Tot. Liq. Prod. | 24.0 | 18.4 | 13.2 | 5.0 | 27.2 | 13.3 | 9.5 |
| $H_2$ | 1.8 | 1.2 | 1.0 | 1.1 | 2.7 | 1.4 | 1.2 |
| $CO/CO_2$ | 0 | 0 | .2 | 0 | 0 | .2 | .2 |
| $CH_4$ | 37.1 | 30.5 | 31.0 | 32.6 | 34.9 | 30.4 | 30.6 |
| $C_2H_6$ | 11.6 | 8.6 | 6.8 | 5.1 | 6.7 | 4.1 | 3.5 |
| $C_2H_4$ | 6.9 | 14.6 | 22.4 | 32.1 | 12.1 | 27.7 | 32.9 |
| $C_3H_8$ | SM | SM | SM | SM | SM | SM | SM |
| $C_3H_6$ | 7.5 | 12.7 | 13.4 | 12.1 | 8.2 | 13.6 | 13.7 |
| $C_4H_{10}$ | 3.4 | 2.8 | .9 | 2.6 | .9 | 1.1 | .9 |
| $C_4H_8$ | 7.7 | 11.2 | 11.1 | 9.4 | 5.5 | 8.2 | 7.5 |
| | | | | | 1.8 | | |
| Total | 100.0 | 100.0 | 100.0 | 100.0 | 100.0 | 100.0 | 100.0 |

A Catalyst treated with $SO_2$ prior to use.
B Cofeed $SO_2$, treat with $SO_2$ first.

Olefins have been prepared from methanol over ZSM-5 with low activity, $SiO_2/Al_2O_3$ 300/1, M. M. Wu and W. W. Kaeding, J. Cat. 88 478 (1984). In the major $C_2$–$C_4$ olefins product, at reasonable conversions, ethylene is usually the smallest component (10–15 wt %). When n-butane was used with these same catalysts, propylene and $C_5$+olefins were produced with only traces of ethylene.

It was surprising to see up to 4.5/1 molar ratios of ethylene/propylene in the product when propane was converted over ZSM-23, Table 2. Catalysts with oxides on silica or alumina such as chromium oxide, gave propylene as the major product. In the initial experiments with ZSM-23, a dramatic increase in ethylene was observed after treatment of the catalyst with $SO_2$. Subsequent work revealed that untreated catalyst also gave high ethylene yields, however, definite but smaller increases (7–10%) resulted from $SO_2$ treatment. Best overall performance with ZSM-23 was observed with a $SiO_2/Al_2O_3$ ratio of 83/1, Table 2.

Since propane is a large volume, fuel-valued hydrocarbon, conversion to $C_2$–$C_4$ olefins, especially ethylene, would give higher value products.

What is claimed is:

1. A process for converting propane to ethylene, said process comprising contacting said propane with a catalyst comprising a crystalline aluminosilicate zeolite ZSM-23 having x-ray diffraction pattern as set forth in Table 1 under conditions sufficient to effect said propane to ethylene conversion.

2. A process according to claim 1, wherein said catalyst further comprises a binder for said ZSM-23.

3. A process according to claim 1, wherein said conversion conditions comprise a temperature of from about 100° C. to about 700° C., a pressure of from about 0.1 atmosphere to about 60 atmospheres, and a weight hourly space velocity of from about 0.5 to about 400.

4. A process for converting propane to ethylene, said process comprising contacting said propane with a catalyst comprising a crystalline aluminosilicate zeolite ZSM-23 having x-ray diffraction pattern as set forth in Table 1 under conditions sufficient to effect said propane to ethylene conversion said ZSM-23 having been contacted with an anhydrous acidic oxide gas capable of accepting hydrogen by reacting therewith, said contacting of ZSM-23 with said acidic oxide taking place prior to contacting said ZSM-23 with said propane under conditions sufficient to increase the yield of ethylene produced from said propane.

5. A process according to claim 4, wherein an anhydrous acid oxide gas capable of accepting hydrogen by reacting therewith is also cofed with said propane for contact with said catalyst, the amount of said acidic oxide cofeed being sufficient to further increase the yield of ethylene produced from said propane.

6. A process according to claim 5, wherein said catalyst further comprises a binder for said ZSM-23.

7. A process according to claim 4, wherein said conversion conditions comprise a temperature of from about 100° C. to about 700° C., a pressure of from about 0.1 atmosphere to about 60 atmospheres, and a weight hourly space velocity of from about 0.5 to about 400.

8. A process according to claim 4, wherein said acidic oxide gas is sulfur dioxide.

9. A process for converting propane to ethylene, said process comprising contacting said propane with a catalyst comprising a crystalline aluminosilicate zeolite ZSM-23 having x-ray diffraction pattern as set forth in Table 1 under conditions sufficient to effect said propane to ethylene conversion wherein an anhydrous acid oxide gas capable of accepting hydrogen by reacting therewith is also cofed with said propane for contact with said catalyst, the amount of said acidic oxide cofeed being sufficient to increase the yield of ethylene produced from said propane.

10. A process according to claim 9, wherein said catalyst further comprises a binder for said ZSM-23.

11. A process according to claim 9, wherein said conversion conditions comprise a temperature of from about 100° C. to about 700° C., a pressure of from about 0.1 atmosphere to about 60 atmospheres, and a weight hourly space velocity of from about 0.5 to about 400.

12. A process according to claim 9, wherein said acidic oxide gas is sulfur dioxide.

13. A process according to claim 1, wherein said ZSM-23 is in the hydrogen form.

* * * * *